US008932624B2

(12) United States Patent
Modak et al.

(10) Patent No.: US 8,932,624 B2
(45) Date of Patent: Jan. 13, 2015

(54) BIO-FILM RESISTANT SURFACES

(75) Inventors: Shanta M. Modak, River Edge, NJ (US); Lauserpina A. Caraos, Hollis, NY (US); Ronald Citron, Blandon, PA (US); Ingrid Geraldo, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 629 days.

(21) Appl. No.: 12/134,911

(22) Filed: Jun. 6, 2008

(65) Prior Publication Data

US 2009/0029961 A1 Jan. 29, 2009

Related U.S. Application Data

(60) Provisional application No. 60/945,288, filed on Jun. 20, 2007.

(51) Int. Cl.
*A61F 13/00* (2006.01)
*A61K 9/70* (2006.01)
*A61L 29/16* (2006.01)
*A01N 47/44* (2006.01)
*A61L 15/46* (2006.01)

(52) U.S. Cl.
CPC ............. *A61L 29/16* (2013.01); *A01N 47/44* (2013.01); *A61L 15/46* (2013.01); *A61L 2300/104* (2013.01)
USPC ...................................................... 424/447

(58) Field of Classification Search
USPC ...................................................... 424/447
See application file for complete search history.

(56) References Cited

U.S. PATENT DOCUMENTS

| | | |
|---|---|---|
| 4,022,605 A | 5/1977 | Konya et al. |
| 4,049,802 A | 9/1977 | Fox, Jr. |
| 4,330,531 A | 5/1982 | Alliger |
| 4,404,197 A | 9/1983 | Fox, Jr. et al. |
| 4,563,485 A | 1/1986 | Fox, Jr. et al. |
| 4,579,731 A | 4/1986 | Fox, Jr. et al. |
| 4,581,028 A | 4/1986 | Fox, Jr. et al. |
| 4,612,337 A | 9/1986 | Fox, Jr. et al. |
| 4,723,950 A | 2/1988 | Lee |
| 4,859,359 A | 8/1989 | DeMatteo et al. |
| 4,867,898 A | 9/1989 | Spaulding et al. |
| 4,956,354 A | 9/1990 | Gutierrez |
| 4,975,217 A | 12/1990 | Brown-Skrobot et al. |
| 5,019,096 A | 5/1991 | Fox, Jr. et al. |
| 5,033,488 A | 7/1991 | Curtis et al. |
| 5,091,442 A | 2/1992 | Milner |
| 5,100,652 A | 3/1992 | Kross et al. |
| 5,180,605 A | 1/1993 | Milner |
| 5,200,194 A | 4/1993 | Edgren et al. |
| 5,209,251 A | 5/1993 | Curtis et al. |
| 5,261,421 A | 11/1993 | Milner |
| 5,310,546 A | 5/1994 | Douglas |
| 5,334,588 A | 8/1994 | Fox, Jr. et al. |
| 5,567,495 A | 10/1996 | Modak et al. |
| 5,614,538 A | 3/1997 | Nelson, Jr. |
| 5,616,338 A | 4/1997 | Fox, Jr. et al. |
| 5,772,640 A | 6/1998 | Modak et al. |
| 5,854,266 A | 12/1998 | Nelson, Jr. |
| 5,891,422 A | 4/1999 | Pan et al. |
| 5,968,539 A | 10/1999 | Beerse et al. |
| 6,075,056 A | 6/2000 | Quigley, Jr. et al. |
| 6,083,208 A | 7/2000 | Modak et al. |
| 6,106,505 A | 8/2000 | Modak et al. |
| 6,120,758 A | 9/2000 | Siddiqui et al. |
| 6,258,368 B1 | 7/2001 | Beerse et al. |
| 6,270,811 B1 | 8/2001 | Fregonese |
| 6,280,758 B1 | 8/2001 | Warren et al. |
| 6,287,583 B1 | 9/2001 | Warren et al. |
| 6,312,675 B1 | 11/2001 | Deane |
| 6,319,958 B1 | 11/2001 | Johnson et al. |
| 6,323,166 B1 | 11/2001 | Kamiya |
| 6,397,224 B1 | 5/2002 | Zubeldia et al. |
| 6,420,326 B1 | 7/2002 | Maile et al. |
| 6,451,748 B1 | 9/2002 | Taylor et al. |
| 6,537,955 B1 | 3/2003 | Raso et al. |
| 6,582,719 B2 * | 6/2003 | Modak et al. .................. 424/430 |
| 6,616,922 B2 | 9/2003 | Taylor et al. |
| 6,630,163 B1 | 10/2003 | Murad |
| 6,632,784 B2 | 10/2003 | Massaux et al. |

(Continued)

FOREIGN PATENT DOCUMENTS

EP 0 054 205 6/1982
EP 0 106 266 4/1984

(Continued)

OTHER PUBLICATIONS

U.S. Appl. No. 11/327,677, filed Jan. 6, 2006.

(Continued)

*Primary Examiner* — Benjamin Packard
(74) *Attorney, Agent, or Firm* — Baker Botts L.L.P.

(57) ABSTRACT

The present invention relates to methods and compositions for rendering a surface resistant to bio-film formation by a combination of an alkanediol and an antimicrobial agent (and, optionally, an organic hydroxy acid). The invention provides for compositions which may be used to render surfaces bio-film resistant, articles having bio-film resistant surfaces, and methods for their preparation. The present invention may be advantageously applied to medical articles as well as articles used in non-medical contexts, such as child care or food preparation.

26 Claims, No Drawings

(56) References Cited

U.S. PATENT DOCUMENTS

| | | |
|---|---|---|
| 6,635,676 B2 | 10/2003 | Baker, Jr. et al. |
| 6,696,399 B1 | 2/2004 | Chernin et al. |
| 6,699,825 B2 | 3/2004 | Rees et al. |
| 6,716,883 B1 | 4/2004 | Casper et al. |
| 6,753,305 B2 | 6/2004 | Raso et al. |
| 6,858,317 B2 | 2/2005 | Aamodt et al. |
| 6,921,745 B2 | 7/2005 | Yamada et al. |
| 6,951,833 B2 | 10/2005 | O'Neil |
| 6,969,522 B2 | 11/2005 | Bessette et al. |
| 6,974,584 B2 | 12/2005 | Bessette |
| 7,435,429 B2 | 10/2008 | Modak et al. |
| 7,563,461 B2 | 7/2009 | Modak et al. |
| 7,563,462 B2 | 7/2009 | Newmark et al. |
| 7,985,773 B2 | 7/2011 | Greten et al. |
| 2001/0010016 A1 | 7/2001 | Modak et al. |
| 2001/0024661 A1 | 9/2001 | Modak et al. |
| 2002/0122876 A1 | 9/2002 | Modak et al. |
| 2002/0165130 A1 | 11/2002 | Johnson et al. |
| 2002/0173775 A1 | 11/2002 | Modak et al. |
| 2002/0192256 A1 | 12/2002 | Wu et al. |
| 2003/0180233 A1 | 9/2003 | Anderson et al. |
| 2003/0195263 A1 | 10/2003 | Schmaus et al. |
| 2003/0213168 A1 | 11/2003 | Hesse et al. |
| 2004/0092482 A1 | 5/2004 | Gupta |
| 2004/0102429 A1 | 5/2004 | Modak et al. |
| 2004/0132667 A1 | 7/2004 | Lintner |
| 2004/0192551 A1 | 9/2004 | Bessette et al. |
| 2004/0247685 A1 | 12/2004 | Modak et al. |
| 2004/0253275 A1 | 12/2004 | Eini et al. |
| 2005/0019431 A1 | 1/2005 | Modak et al. |
| 2005/0026802 A1 | 2/2005 | Kilkenny et al. |
| 2005/0048139 A1 | 3/2005 | Modak et al. |
| 2005/0222276 A1 * | 10/2005 | Schmaus et al. ............... 514/738 |
| 2005/0238602 A1 | 10/2005 | Modak et al. |
| 2006/0018867 A1 | 1/2006 | Kawasaki et al. |
| 2006/0051384 A1 | 3/2006 | Scholz et al. |
| 2006/0099237 A1 | 5/2006 | Modak et al. |
| 2006/0198800 A1 | 9/2006 | Dilallo et al. |
| 2006/0216246 A1 | 9/2006 | Belanger et al. |
| 2006/0233901 A1 | 10/2006 | Jamieson et al. |
| 2006/0293201 A1 | 12/2006 | Simon et al. |
| 2006/0293214 A1 | 12/2006 | Cheng et al. |
| 2007/0003538 A1 | 1/2007 | Madhyastha |
| 2007/0014823 A1 | 1/2007 | Iwata et al. |
| 2007/0020342 A1 | 1/2007 | Modak et al. |
| 2007/0027119 A1 | 2/2007 | Ahmed et al. |
| 2007/0190094 A1 | 8/2007 | Bessette et al. |
| 2007/0275070 A1 | 11/2007 | Ahmed et al. |
| 2008/0008729 A1 | 1/2008 | Swaine et al. |
| 2008/0038219 A1 | 2/2008 | Mosbaugh et al. |
| 2008/0063607 A1 | 3/2008 | Tamarkin et al. |
| 2008/0234173 A1 | 9/2008 | Warr et al. |
| 2008/0253976 A1 | 10/2008 | Scott et al. |
| 2008/0299220 A1 | 12/2008 | Tamarkin et al. |
| 2008/0318784 A1 | 12/2008 | Koo et al. |
| 2009/0004122 A1 | 1/2009 | Modak et al. |
| 2009/0035228 A1 | 2/2009 | Modak et al. |
| 2009/0068255 A1 | 3/2009 | Yu et al. |
| 2009/0088358 A1 | 4/2009 | Roso et al. |
| 2009/0191288 A1 | 7/2009 | Squires et al. |
| 2010/0034871 A1 | 2/2010 | Mikkelsen et al. |
| 2010/0140368 A1 | 6/2010 | De Lame et al. |
| 2010/0172848 A1 | 7/2010 | Modak et al. |
| 2010/0183524 A1 | 7/2010 | Zielinski et al. |
| 2010/0196494 A1 | 8/2010 | Van Beek |
| 2010/0216889 A1 | 8/2010 | Modak et al. |
| 2010/0234460 A1 | 9/2010 | Foret et al. |
| 2010/0248962 A1 | 9/2010 | Wilczynski et al. |
| 2010/0317743 A1 | 12/2010 | Macinga et al. |
| 2010/0323043 A1 | 12/2010 | Perla et al. |
| 2011/0028563 A1 | 2/2011 | Found |
| 2011/0070376 A1 | 3/2011 | Wales et al. |
| 2011/0142899 A1 | 6/2011 | Lagaron Abello et al. |
| 2012/0100231 A1 | 4/2012 | Perla et al. |
| 2012/0129950 A1 | 5/2012 | Macinga et al. |
| 2012/0201902 A1 | 8/2012 | Modak et al. |
| 2013/0230609 A1 | 9/2013 | Modak et al. |

FOREIGN PATENT DOCUMENTS

| | | | |
|---|---|---|---|
| EP | 1 146 112 | 10/2001 | |
| EP | 1 288 285 | 3/2003 | |
| FR | 2771632 | 6/1999 | |
| GB | 1 060 447 | 3/1967 | |
| JP | 2002370958 | 12/2002 | |
| JP | 2004-217615 | 8/2004 | |
| JP | 04250331 A1 * | 9/2004 | ............ A01N 31/02 |
| JP | 2004-322078 | 11/2004 | |
| KR | 10-2004-077206 | 9/2004 | |
| SU | 513676 | 5/1976 | |
| WO | WO 84/04556 | 11/1984 | |
| WO | WO 85/01208 | 3/1985 | |
| WO | WO 89/06962 | 8/1989 | |
| WO | WO 92/04029 | 3/1992 | |
| WO | WO 93/02717 | 2/1993 | |
| WO | WO 98/51273 | 11/1998 | |
| WO | WO 99/22718 | 5/1999 | |
| WO | WO 01/72262 | 10/2001 | |
| WO | WO 02/22060 | 3/2002 | |
| WO | WO/03/000303 | 1/2003 | |
| WO | WO 03/018498 | 3/2003 | |
| WO | WO 03/018743 | 3/2003 | |
| WO | WO 03/077856 | 9/2003 | |
| WO | WO 03/078367 | 9/2003 | |
| WO | WO 2004/004631 | 1/2004 | |
| WO | WO 2004014416 | 2/2004 | |
| WO | WO/2006/010269 | 2/2006 | |
| WO | WO 2006/023349 | 3/2006 | |
| WO | WO 2006099359 | 9/2006 | |
| WO | WO 2007/069214 | 6/2007 | |
| WO | WO 2007/071089 | 6/2007 | |
| WO | WO 2007/077573 | 7/2007 | |
| WO | WO 2007/095041 | 8/2007 | |
| WO | WO 2007/101848 | 9/2007 | |
| WO | WO 2007/123790 | 11/2007 | |
| WO | WO 2007/126651 | 11/2007 | |
| WO | WO 2008/031087 | 3/2008 | |
| WO | WO 2008/042197 | 4/2008 | |
| WO | WO 2008/061187 | 5/2008 | |
| WO | WO 2008/119841 | 10/2008 | |
| WO | WO 2008/154395 | 12/2008 | |
| WO | WO 2008/157847 | 12/2008 | |
| WO | WO 2009/062746 | 3/2009 | |
| WO | WO 2009/049208 | 4/2009 | |
| WO | WO 2010/091415 | 8/2010 | |
| WO | WO 2010/119369 | 10/2010 | |
| WO | WO 2011/002929 | 1/2011 | |
| WO | WO 2011/0151835 | 12/2011 | |
| WO | WO 2012/017349 | 2/2012 | |
| WO | WO 2012/051204 | 4/2012 | |

OTHER PUBLICATIONS

U.S. Appl. No. 12/016,788, filed Jan. 18, 2008.
U.S. Appl. No. 12/134,918, filed Jun. 6, 2008.
U.S. Appl. No. 12/136,530, filed Jun. 10, 2008.
U.S. Appl. No. 12/367,851, filed Feb. 9, 2009.
U.S. Appl. No. 12/136,530, Sep. 22, 2009 Non-Final Office Action.
U.S. Appl. No. 12/136,530, Dec. 11, 2009 Response to Non-Final Office Action.
U.S. Appl. No. 11/327,677, Jun. 1, 2009 Non-Final Office Action.
U.S. Appl. No. 11/327,677, Aug. 27, 2009 Response to Non-Final Office Action.
U.S. Appl. No. 11/327,677, Nov. 2, 2009 Notice of Allowance.
Bezic et al.; 2003; "Composition and antimicrobial activity of *Achillea clavennae* L. essential oil." Phytother. Res. 17(9):1037-1040.
Bion, 2008; "Acne Treatment Products" http://www.bion-research.com/acne_treatment_products.htm.
Bion, 2008; "Moderate to Severe Acne" http://www.bion-research.com/moderate_to_severe_acne.htm.
Brehm-Stecher et al.; 2003; "Sensitization of *Staphylococcus aureus*

(56) References Cited

OTHER PUBLICATIONS and *Escherichia coli* to antibiotics by the sesquiterpenoids nerolidol, farnesol, bisabolol, and apritone."Antimicrobial Agents and Chemotherapy; 47(10):3357-3360.
de Abreu Gonzaga et al.; 2003; "Composition and antibacterial activity of the essential oils from *Zanthoxylum rhoifolium*." Planta Med. 69(8):773-775.
Garcia et al.; 2003; "Virucidal activity of essential oils from aromatic plants of San Luis, Argentina." Phytother. Res. 17(9):1073-1075.
Goren et al.; 2003; "Analysis of essential oil of *Coridothymus capitatus* (L.) and its antibacterial and antifungal activity." Z. Naturforsch. 58(9-10):687-690.
Hajhashemi et al.; 2003; "Anti-inflammatory and analgesic properties of the leaf extracts and essential oil of *Lavandula angustifolia* Mill." J. Ethnopharmacol. 89(1):67-71.
Minami et al.; 2003; "The inhibitory effect of essential oils on herpes simplex virus type-1 replication in vitro." Microbial Immunol. 47(a):681-684.
Paranagama et al.; 2003; "Fungicidal and anti-aflatoxigenic effects of the essential oil of *Cymbopogon citratus* (DC.) Stapf. (lemongrass) against *Aspergillus flavus* Link. isolated from stored rice." Lett. Appl. Microbiol.; 37(1):86-90.
Schuhmacher et al.; 2003; "Virucidal effect of peppermint oil on the enveloped viruses herpes simplex virus type 1 and type 2 in vitro." Phytomedicine 10:504-510.
Shin; 2003; "Anti-*Aspergillus* activities of plant essential oils and their combination effects with ketoconazole or amphotericin B." Arch. Pharm. Res. 26(5):389-393.
Silva et al.; 2003; "Analgesic and anti-inflammatory effects of essential oils of *Eucalyptus*." J. Ethnopharmacol. 89(2-3);277-283.
Valero and Salmera; 2003; "Antibacterial activity of 11 essential oils against *Bacillus cereus* in tyndallized carrot broth." Int. J. Food Microbiol. 85(1-2):73-81.
Velluti et al.; 2003; "Inhibitory effect of cinnamon, clove, lemongrass, oregano and palmarose essential oils on growth and fumonisin B1 production by *Fusarium proliferatum* in maize grain." Int. J. Food Microbiol.; 89:145-154.
U.S. Appl. No. 12/694,119, filed Jan. 26, 2010.
U.S. Appl. No. 12/694,141, filed Jan. 26, 2010.
U.S. Appl. No. 12/136,530, Jun. 16, 2010 Non-Final Office Action.
U.S. Appl. No. 12/136,530, Jun. 2, 2010 RCE and Response to Final Office Action.
U.S. Appl. No. 12/136,530, Mar. 2, 2010 Final Office Action.
Pommier, et al, "Phase III Randomized Trial of Calendula Officinalis Compared With Trolamine for the Prevention of Acute Dermatitis During Irradiation for Breast Cancer," J Clin Oncol:1447-1453, Apr. 15, 2004, p. 1447, Results, Conclusion.
Baiju et al., 2008, "Development of a Novel Surface Disinfectant Composition Containing Essential Oils and Fruit Acid Against Nosocomial Pathogens Commonly Associated with Environmental Surfaces," *International Journal of Essential Oil Therapeutics*, vol. 2; p. 9-14.
Gershon, et al., 2006, "Antifungal Properties of *n*-Alkanols, α, *w-n*-Alkanedoils, and *w*-Chloro-α-alkanols," *J. Pharm. Sci.*, vol. 64, No. 4: p. 381-384.
Kupferwasser, et al., 1999, "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects," *Circulation*, vol. 99: p. 2791-2797.
Kupferwasser, et al., 2003, "Salicylic Acid Attenuates Virulence in Endovascular Infections by Targeting Global Regulatory Pathways in *Staphylococcus aureus*," *Clin. Invest.*, vol. 112, No. 2: p. 222-233.
U.S. Appl. No. 12/136,530, Jun. 29, 2011 Non-Final Office Action.
U.S. Appl. No. 12/136,530, May 19, 2011 Amendment and Request for Continued Examination (RCE).
U.S. Appl. No. 12/136,530, Nov. 19, 2010 Final Office Action.
U.S. Appl. No. 12/136,530, Sep. 15, 2010 Response to Non-Final Office Action.
U.S. Appl. No. 12/016,788, Oct. 24, 2011 Non-Final Office Action.
Entry for "citral" in Merck Index, 14th Edition.
Ziya Al-Din Abdullah Ibn Al-Baitar; Al-Jaam'e-li-Mufradaat-al-Advia-wal-Aghzia, vol. IV (13th century AD), Matba Amra, Cario, Egypt, 1874 AD p. 57.
Abu Bakr Mohammad, Bin Zakariyya Al-Razi; Kitaab-al-Haawi-fil-Tibb, vol. ii (9th century AD), Dayerah-Al-Ma'aarof Is,amoa. Juderabad. 1976 AD p. 434.
Mohammad Shareef Khan; Ilaaj-al-Amraaz (18th centruy AD), Afzal-al-Matabe, Barqi Press, Delhi, 1921 AD p. 335.
Mohammad Azam Khan; Muheet-e-Azam vol. III (19th century AD), Matba Nizami, Kanpur, 1887 AD p. 69.
Mohammad Najmul Ghani Khan; Khazaain-al-Advia, vol. II (20th century Ad), Nadeem Yunus Printer/Sheikh Mohd Basheer & Sons, Lahore, 1911 AD p. 657.
Mohammad Azam Khan; Muheet-e-Azam vol. I (19th century AD), Matba Nizami, Kanpur, 1896 AD p. 257.
Cakrapanidattah; Cakradattah—Translated by Indradeva Tripathi; Chaukhamba Sanskrit Samsthan (Varanasi), Ed. 4th 2002, p. 260.
U.S. Appl. No. 12/016,788, Aug. 1, 2013 Non-Final Office Action.
U.S. Appl. No. 13/335,363, Nov. 1, 2013 Final Office Action.
U.S. Appl. No. 13/335,363, Aug. 15, 2013 Response to Non-Final Office Action.
U.S. Appl. No. 13/412,464, Sep. 19, 2013 Notice of Non-Compliant.
U.S. Appl. No. 13/412,464, Aug. 8, 2013 Response to Restriction Requirement.
Nazer, et al., "Combinations of food antimicrobials at low levels to inhibit the growth of *Salmonella* sv. Typhimurium: a synergistic effect?", *Food Microbiology* 22:391-398 (2005).
U.S. Appl. No. 13/335,363, Feb. 19, 2013 Non-Final Office Action.
U.S. Appl. No. 13/412,464, Feb. 8, 2013 Restriction Requirement.
U.S. Appl. No. 12/016,788, Feb. 22, 2013 Amendment and Request for Continued Examination (RCE).
Choudhary, et al., "Solvent-free selective oxidation of benzyl alcohol and benzaldehyde by *tert*-butyl hydroperoxide using $MnO_4$-exchanged Mg-Al-hydrotalcite catalsysts", *Catalysis Letters*, 86(4):229-233 (2003).
Zhang, et al., "Antifungal Activities of Major Tea Leaf Volatile Constituents toward Colletorichum Camelliae Massea", Journal of Agricultural and Food Chemistry, 54(11):3936-3940 (2006).
U.S. Appl. No. 14/267,606, filed May 1, 2014.
U.S. Appl. No. 14/267,403, filed May 1, 2014.
U.S. Appl. No. 14/294,933, filed Jun. 3, 2014.
U.S. Appl. No. 12/694,119, Jun. 26, 2014 Non-Final Office Action.
U.S. Appl. No. 12/016,788, Jun. 19, 2014 Final Office Action.
U.S. Appl. No. 13/335,363, Apr. 1, 2014 Amendment and Request for Continued Examination (RCE).
U.S. Appl. No. 13/412,464, Jul. 7, 2014 Response to Non-Final Office Action.
U.S. Appl. No. 12/134,918, May 7, 2014 Response to Non-Final Office Action.
Cowan, "Plant product as antimicrobial agents", *Clinical Microbiology Reviews*, 12(4):564-582 (1999).
Nannapaneni et al., "Antimicrobial activity of commercial citrus-based natural extracts against *Escherichia coli* O157:H7 isolates and mutant strains", *Foodborne Pathog Dis.*, 5(5):695-699 (2008).
International Search Report and Written Opinion for PCT/US2013/071731, dated Feb. 12, 2014.
Keeven et al., "Evaluating the preservative effectiveness of RGP lens care solutions", *The Contact Lens Association of Ophthalmologists Journal*, 21(4):238-241 (1995).
El-Zemity et al., "Antifungal activity of some essential oils and their major chemical constituents against some phytopathogenic fungi", *Journal of Pest Control and Enviromental Science*, 13(1):87-99 (2005).
U.S. Appl. No. 12/134,918, Jul. 31, 2012 Final Office Action.
U.S. Appl. No. 12/694,141, Jul. 24, 2012 Final Office Action.
Judžentiené, et al,, "Characterisitcs of essential oil composition in the needles of young Scots pine (*Pinus sylvestris* L.) stands growing along an aerial ammonia gradient", *Chemija*, 17(4):67-73, 2006.
Entry for Lemongrass oil, downloaded Jul. 15, 2012 from internet site: https://www.essentialoils.co.za/essential-oils/lemongrass.htm.
Entry for Orange Oil, downloaded Jul. 15, 2012 from internet site: https://www.essentialoils.co.za/essential-oils/orange.htm.

(56) References Cited

OTHER PUBLICATIONS

Kurita, et al., "Synergistic Antimicrobial Effect of Ehtanol, Sodium Chloride, Acetic Acid and Essentail Oil Components", *Agricultural Biology Chemistry*, 47(1):67-75, 1983.

U.S. Appl. No. 12/134,918, Nov. 7, 2013 Non-Final Office Action.

"Sheer Moisturizer Hand Sanitizer", *Mintel Global New Products Database*, pp. 1-4 (2010) Retrieved from the Internet: URL:www.gnpd.com [Retrieved on Aug. 34, 2013].

"Antibacterial Wet Wipes", *Mintel Global New Products Database*, pp. 1-2 (2008) Retrieved from the Internet: URL:www.gnpd.com [Retrieved on Sep. 24, 2013].

U.S. Appl. No. 12/134,918, Mar. 28, 2012 Response to Non-Final Office Action.

U.S. Appl. No. 12/134,918, Nov. 15, 2011 Non-Final Office Action.

U.S. Appl. No. 12/694,141, Mar. 28, 2012 Response to Non-Final Office Action.

U.S. Appl. No. 12/694,141, Nov. 28, 2011 Non-Final Office Action.

U.S. Appl. No. 13/412,464, filed Mar. 5, 2012.

U.S. Appl. No. 12/694,119, Dec. 21, 2012 Amendment and Request for Continued Examination (RCE).

U.S. Appl. No. 12/134,918, Jan. 31, 2013 Amendment and Request for Continued Examination (RCE).

Ayliffe, et al., "Hand disinfection: A comparison of various agents in laboratory and ward studies", *Journal of Hospital Infection*, 11(3):226-243 (1988).

Fox, et al., "Comparative evaluation of zinc sulfadiazine and silver sulfadiazine in burn wound infection", *J. Burn Care Rehabil.*, 11(2):112-117 (1990).

Gaonkar, et al., "In vivo efficacy of an alcohol-based surgical hand disinfectant containing a synergistic combination of ethylhexylglycerin and preservatives", *Journal of Hospital Infection*, 63(4):412-417 (2006).

Gaonkar, et al., "An alcohol hand rub containing a synergistic combination of an emollient and preservatives: prolonged activity against transient pathogens", *Journal of Hospital Infection*, 59(1):12-18 (2005).

European Supplementary Search Report for EP 08780771.5, dated Dec. 17, 2012.

International Search Report and Written Opinion for PCT/US2012/052793, dated Nov. 19, 2012.

International Search Report and Written Opinion for PCT/US2012/063013, dated Jan. 4, 2013.

International Search Report and Written Opinion for PCT/US2012/037135, dated Oct. 16, 2012.

U.S. Appl. No. 12/694,119, Oct. 12, 2011 Non-Final Office Action.

Entry for "citral" in Merck Index, 14th Edition, 2006.

Mohammad Najmul Ghani Khan; Khazaain-al-Advia, vol. II (20th century AD), Nadeem Yunus Printer/Sheikh Mohd Basheer & Sons, Lahore, 1911 AD p. 656.

Mohammad Najmul Ghani Khan; Qaraabaadeen Najm-al-Ghani (20th century AD), Munshi Nawal Kishore, Lucknow, (Second Edition) 1928 AD p. 566.

Mohammad Azam Khan; Muheet Azam vol. II (Part II) (19th century AD), Matba Nizami, Kanpur, 1898 AD p. 3.

Susruta; Susruta Samhita—Edited & translated by P.V. Sharma, vol. III: Chaukhamba Visvabharati, Varanasi, Edn. Ist, 2001. [Time of origin 1000 BC—5th century] p. 10.

Mohammad Azam Khan; Muheet-e-Azam vol. III (19th century AD), Matba Nizami, Kanpur, 1887 AD p. 261.

Mohammad Shareef Khan; Ilaaj-al-Amraaz (18th centruy AD), Afzal-al-Matabe, Barqi Press, Delhi, 1921 AD p. 357.

Siddhayogasamgrahah—Compiled by Yadavji Trikamji Acharya, Sri Baidyanath Ayurved Bhawan, Allahabad, Edn. 1st 1978 pp. 131-132.

Mohammad Najmul Ghani Khan; Khazaain-al-Advia, vol. III (20th century AD), Nadeem Yunus Printer/Sheikh Mohd Basheer & Sons, Lahore, 1926 AD p. 568.

Sarngadharacarya; Saringadhara Samhita—Translated by Smt. Shailaja Srivastava: Chaukhamba Orientalia, Varansai, Edn. 2nd, 1998. [Time of origin 13th century] pp. 431-432.

U.S. Appl. No. 13/335,363, filed Dec. 22, 2011.

U.S. Appl. No. 12/016,788, Apr. 24, 2012 Response to Non-Final Office Action.

U.S. Appl. No. 12/016,788, Aug. 24, 2012 Final Office Action.

Bettini Mercia de Fatima M., "Purification of Orange Peel Oil and Oil Phase by Vacuum Distillation", *Functional Food Ingerdients and Nutraceuticals, Processing Technologies*, Edited by John Shi, CRC Press 2006, pp. 157-172.

Cancio, et al., "Burn wound infections" In: *Surgical Treatment: Evidence-Based and Problem-Oriented*, 2001.

Fang, et al., "Prospective clinical study of Hydron, a synthetic dressing, in delivery of an antimicrobial drug to second-degree burns", *J. Burn Care Rehabil.*, 8(3):206-209 (1987).

\* cited by examiner

BIO-FILM RESISTANT SURFACES

PRIORITY CLAIM

This application claims priority to U.S. Provisional Application Ser. No. 60/945,288 filed Jun. 20, 2007, the contents of which are hereby incorporated in their entireties herein.

GRANT INFORMATION

Not applicable.

1. INTRODUCTION

The present invention relates to methods and compositions for rendering a surface resistant to bio-film formation by a combination of an alkanediol and an antimicrobial agent (and, optionally, an organic hydroxy acid).

2. BACKGROUND OF THE INVENTION

Whenever a medical article comes in contact with a patient, a risk of infection is created. Thus, a contaminated examination glove, tongue depressor, or stethoscope could transmit infection. The risk of infection dramatically increases for invasive medical articles, such as intravenous catheters, arterial grafts, endotracheal or intracerebral shunts and prosthetic devices, which not only are, themselves, in intimate contact with body tissues and fluids, but also create a portal of entry for pathogens.

A number of methods for reducing the risk of infection have been developed which incorporate anti-infective compounds into medical articles. Ideally, such articles provide effective levels of an anti-infective compound during the entire period that the article is being used. This sustained release may be problematic to achieve, in that a mechanism for dispersing an anti-infective compound over a prolonged period of time may be required, and the incorporation of sufficient amounts of anti-infective compound may adversely affect the surface characteristics of the article. The difficulties encountered in providing effective anti-microbial protection increase with the development of drug-resistant pathogens.

Two well known anti-infective compounds are chlorhexidine and triclosan. The following patents and patent applications relate to the use of anti-microbial compounds in medical articles.

U.S. Pat. No. 4,723,950 by Lee relates to a microbicidal tube which may be incorporated into the outlet tube of a urine drainage bag. The microbicidal tube is manufactured from polymeric materials capable of absorbing and releasing anti-microbial substances in a controllable, sustained, time-release mechanism, activated upon contact with droplets of urine, thereby preventing the retrograde migration of infectious organisms into the drainage bag. The microbicidal tube may be produced by one of three processes: (1) a porous material, such as poly-propylene, is impregnated with at least one microbicidal compound, and then coated with a hydrophilic polymer which swells upon contact with urine, causing the leaching-out of the microbicidal compound; (2) a porous material, such as high density polyethylene, is impregnated with a hydrophilic polymer and at least one microbicidal compound; and (3) a polymer, such as silicone, is compounded and co-extruded with at least one microbicidal compound, and then coated with a hydrophilic polymer. A broad range of microbicidal compounds are disclosed, including chlorhexidine and triclosan, and combinations thereof. The purpose of Lee's device is to allow the leaching out of microbicidal compounds into urine contained in the drainage bag; similar leaching of microbicidal compounds into the bloodstream of a patient may be undesirable.

U.S. Pat. No. 5,091,442 by Milner relates to tubular articles, such as condoms and catheters, which are rendered antimicrobially effective by the incorporation of a non-ionic sparingly soluble antimicrobial compound, such as triclosan. The tubular articles are made of materials which include natural rubber, polyvinyl chloride and polyurethane. Antimicrobial compound may be distributed throughout the article, or in a coating thereon. A condom prepared from natural rubber latex containing 1% by weight of triclosan, then dipped in an aqueous solution of chlorhexidine, is disclosed. U.S. Pat. Nos. 5,180,605 and 5,261,421, both by Milner, relate to similar technology applied to gloves.

U.S. Pat. Nos. 5,033,488 and 5,209,251, both by Curtis et al, relate to dental floss prepared from expanded polytetrafluoroethylene (PTFE) and coated with microcrystalline wax. Antimicrobial compounds such as chlorhexidine or triclosan may be incorporated into the coated floss.

U.S. Pat. No. 5,200,194 by Edgren et al. relates to an oral osmotic device comprising a thin semipermeable membrane wall surrounding a compartment housing a "beneficial agent" (that is at least somewhat soluble in saliva) and a fibrous support material composed of hydrophilic water-insoluble fibers. The patent lists a wide variety of "beneficial agents" which may be incorporated into the oral osmotic device, including chlorhexidine and triclosan.

International Patent Application No. PCT/GB92/01481, Publication No. WO 93/02717, relates to an adhesive product comprising residues of a co-polymerizable emulsifier comprising a medicament, which may be povidone iodine, triclosan, or chlorhexidine.

U.S. Pat. Nos. 5,019,096 and 5,616,338, both by Fox, Jr. et al. relate to infection-resistant medical articles comprising a synergistic combination of a silver compound (such as silver sulfadiazine) and chlorhexidine and their methods of manufacture, respectively. U.S. Pat. No. 5,334,588 by Fox, Jr. et al. relates to methods of inhibiting transmission of Hepatitis B virus using compositions comprising silver sulfadiazine and preferably further comprising a biguanide such as chlorhexidine and/or a detergent such as sodium deoxycholate.

U.S. Pat. Nos. 5,567,495, 5,772,640, 6,083,208 and 6,106,505 and U.S. patent publication Ser. Nos. 2001/0010016, 2001/0024661, 2002/0122876 and 2002/0173775, all by Modak et al., provide inter alia for anti-infective medical devices, either hydrophobic or hydrophilic, impregnated, coated, or impregnated and coated with various combinations of chlorhexidine, a silver salt such as silver sulfadiazine, silver oxide, silver carbonate or silver nitrate among others, a bismuth salt such as bismuth nitrate, bismuth citrate or bismuth salicylate among others, a zinc salt, a cerium salt, triclosan, combinations of chlorhexidine free base and chlorhexidine acetate, benzalkonium chloride, citrate, povidone iodine, parachlorometaxylene, gramicidin, polymixin, norfloxacin, tobramycin, sulfamylon, polyhexamethylene biguanide, alexidine, iodine, rifampicin, miconazole, bacitracin, and minocycline.

United States Patent Application Publication No. US 20060099237 A1 relates to combinations of octoxyglycerin and anti-infective compounds that synergistically increase the anti-infective properties of medical articles impregnated and/or coated with various combinations of octoxyglycerin and anti-infective compounds relative to the anti-infective properties of medical articles impregnated and/or coated with the same anti-infective compounds without octoxyglycerin.

Salicylic acid, an organic β-hydroxy acid, traditionally used as an antithrombogenic agent, has been recently shown to affect bacterial infection and virulence. In endocarditis, *Staphylococcus aureus* causes endovascular infections, damaging endothelial cells of valvular tissue. Salicylic acid appears to mitigate the virulent effects, reducing growth and cellular density of *S. aureus*-induced infective endocarditis in an animal model (Kupferwasser et al., 1999 "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects," Circulation, 99:2791-2797; Kupferwasser et al., "Salicylic acid attenuates virulence in endovascular infections by targeting global regulatory pathways in *Staphylococcus aureus*," J Clin Invest. 2003; 112(2):222-33). In fact, salicylic acid modulates virulence by suppressing expression of adherence factors (Kupferwasser et al., "Salicylic acid attenuates virulence in endovascular infections by targeting global regulatory pathways in *Staphylococcus aureus*," J Clin Invest. 2003; 112(2): 222-33).

U.S. Pat. No. 6,582,719, International Patent Application No. PCT/US02/03087, and pending U.S. patent application Ser. No. 10/633,204, filed Jul. 30, 2003, all of which are incorporated by reference, disclose antimicrobial compositions comprising antiseptics, such as chlorhexidine, triclosan, and benzalkonium chloride, and antibiotics, such as minocycline, which may be particularly useful against antibiotic-resistant microorganisms. It has been discovered, however, that although certain of the chlorhexidine-containing solutions exhibited a broad spectrum of activity against many organisms, the solutions became unstable, forming precipitates after a few days at room temperature. Having a short shelf life limits the application of these compositions in coating and impregnating medical devices.

Alkanediols are emollient solvents used in various applications, including in the cosmetics industry. Alkanediols are reported to have anti-fungal activity (Gershon, 2006, J. Pharm. Sci. 69(4):381-384).

3. SUMMARY OF THE INVENTION

The present invention relates to methods and compositions for rendering a surface resistant to bio-film formation by a combination of an alkanediol and an antimicrobial agent (and, optionally, an organic hydroxy acid). It is based, at least in part, on the discovery that a combination of octanediol, chlorhexidine, and lactic acid was observed to inhibit the adherence of certain bacteria and yeast to a catheter surface.

In one set of non-limiting embodiments, the present invention provides for compositions which may be used to render a surface resistant to bio-film formation. Such compositions may be solutions for impregnating or coating an article, or wipes comprising such solutions.

In another set of non-limiting embodiments, the present invention provides for methods of rendering a surface resistant to bio-film formation which utilize the aforementioned solutions or wipes.

In yet another set of non-limiting embodiments, the present invention provides for articles having a bio-film resistant surface created according to the invention.

The present invention may be used in the context of surfaces of medical articles or other surfaces which are desirably protected from microbe adherence, such as surfaces in an environment associated with child care, food preparation, etc.

4. DETAILED DESCRIPTION OF THE INVENTION

For clarity of description and not by way of limitation, the detailed description of the invention is divided into the following subsections:
(i) antimicrobial agents;
(ii) alkanediols;
(iii) hydroxy acids;
(iv) compositions for preparing a bio-film resistant surface;
(v) methods for producing a bio-film resistant surface; and
(vi) articles having a bio-film resistant surface.

"Bio-film resistant" as that term is used herein means that adherence of a microbe to the surface is inhibited.

4.1 Antimicrobial Agents

The present invention utilizes one or more biguanide, including, but not limited to, chlorhexidine, either as a free base, or a salt thereof, or a combination of free base and a chlorhexidine salt. Non-limiting examples include chlorhexidine diphosphanilate, chlorhexidine digluconate, chlorhexidine diacetate (also known as chlorhexidine acetate or CHA), chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluoro-phosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-.alpha.-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynaphthoate, and chlorhexidine embonate and combinations thereof. Other examples of biguanides are polyhexamethylene biguanide and alexidine biguanide.

Other antimicrobial agents which may, in addition to a biguanide, be used according to the invention include, but are not limited to, triclosan, phenoxyethanol, a tetracycline compound such as minocycline, polymixin, octoxyglycerine, a chlorinated phenol such as parachlorometaxylenol and a quaternary ammonium compound such as benzalkonium chloride or benzethonium chloride. Combinations of such agents may also be used.

In preferred non-limiting embodiments, an antimicrobial agent to be used together with a biguanide is a silver compound. The term silver compound, as used herein, refers to a compound comprising silver, either in the form of a silver atom or a silver ion unlinked or linked to another molecule via a covalent or noncovalent (e.g. ionic) linkage, including but not limited to covalent compounds such as silver sulfadiazine ("AgSD") and silver salts such as silver oxide ("$Ag_2O$"), silver carbonate ("$Ag_2CO_3$"), silver deoxycholate, silver salicylate, silver iodide, silver nitrate ("$AgNO_3$"), silver paraminobenzoate, silver paraminosalicylate, silver acetylsalicylate, silver ethylenediaminetetraacetic acid ("AgEDTA"), silver picrate, silver protein, silver citrate, silver lactate and silver laurate and combinations thereof.

4.2 Alkanediols

Examples of alkanediols which may be used, according to the invention, include alkanediols having between about five and twenty-five carbon atoms in the backbone, including but not limited to pentanediol, hexanediol, heptanediol, octanediol, nonanediol, decanediol, undecanediol, dodecanediol, cyclodecanediol, tridecanediol tetradecanediol, pentanedecanediol, hexadecanediol, heptadecanediol, octadecanediol, nonadecanediokl, eicosanediol, heneicosanediol, docosanediol, tricosanediol, and pentacosanediol, where the preferred alkanediols include 1,2 decanediol, 1,10 decanediol, 1,2 dodecanediol, 1,12 dodecanediol, cyclododecanediol, 1,13 tridecanediol, 1,2 tetradecanediol, 1,14 tetradecanediol, and especially preferred are 1,2 decanediol, 1,2 dodecanediol, 1,12 dodecanediol, and 1,2 tetradecanediol.

4.3 Hydroxy Acids

Organic hydroxy acids which may be used according to the invention include α-hydroxy acids as well as β-hydroxy acids. Non-limiting examples of such hydroxyacids include α-hydroxy acids such as lactic acid, glycolic acid, and citric acid and β-hydroxy acids such as salicylic acid, betahydroxybutanoic acid, tropic acid, and trethocanic acid.

4.4 Compositions for Preparing a Bio-Film Resistant Surface

The present invention provides for compositions that may be used to prepare a bio-film resistant surface.

In a particular set of non-limiting embodiments, the present invention provides for a composition for preparing a bio-film resistant surface comprising a biguanide, an alkanediol, and a solvent, where the biguanide is present at between about 0.1 and 5 percent (weight/volume), or between about 2.5 and 4 percent (weight/volume), or between about 0.5 and 3 percent (weight/volume), and the alkanediol is present at between about 0.5 and 5 percent (volume/volume), and the solvent is selected from the group consisting of an alcohol (e.g. methanol, ethanol, isopropanol, and mixtures thereof) and tetrahydrofuran. In preferred non-limiting embodiments of the invention, the biguanide is chlorhexidine, such as chlorhexidine free base, chlorhexidine diacetate, chlorhexidine gluconate, or a mixture thereof, and the alkanediol is octanediol. Such compositions may further comprise one or more additional antimicrobial agent (in an amount between about 0.05 and 3 percent, preferably between about 0.2 and 1.5 percent (weight/volume), one or more hydroxy acid (in an amount between about 0.5 and 3 percent, preferably between about 0.2 and 2 percent (volume/volume), and/or one or more polymer (in an amount between about 1 and 3 percent or between about 1 and 20 percent or between about 1 and 10 percent, or between about 3 and 6 percent (weight/volume). In preferred non-limiting embodiments, the additional antimicrobial agent may be a silver compound, such as, but not limited to, silver sulfadiazine, the hydroxy acid may be lactic acid, and/or the polymer may be 93A polyurethane, 60D polyurethane, silastic medical adhesive type A, or a mixture thereof.

The term "about", as used throughout this document, means plus or minus 20 percent of the recited value.

The term "percent (weight/volume)" means the [weight of the referenced substance divided by the volume of the composition] multiplied by 100, or, in other words, the number of grams of the referenced substance in 100 milliliters of the composition.

As a specific non-limiting example, 100 ml of a composition comprising A percent biguanide (weight/volume), B percent alkanediol (volume/volume), C percent organic acid (volume/volume), D percent polymer (weight/volume) and E percent non-biguanide antimicrobial (weight/volume), in a solvent (which can be a mixed solvent), may be prepared by providing A grams of biguanide, D grams of polymer, E grams of non-biguanide antimicrobial, B mls of liquid form (e.g. melted) of alkanediol, and C mls of organic acid, adding each of these to solvent to form a solution and then solvent may be used to bring the total volume of the composition to 100 ml.

In non-limiting embodiments of the invention, a composition may be prepared by (i) dissolving biguanide, alkanediol, and optionally organic acid in an alcohol such as ethanol or methanol; (ii) dissolving polymer in tetrahydrofuran or equivalent solvent; and then (iii) mixing the solutions prepared in (i) and (ii).

In specific, non-limiting examples, the present invention provides for the following impregnation solutions, which may be used, not by way of limitation, to impregnate catheters such as polyurethane catheters, and also provides for medical articles, such as catheters (e.g. polyurethane catheters) impregnated therewith:

2% CHX+1.5% CHA+0.75% AgSD+1% Lactic acid+3% 93A PU+1% 60D PU+30% Methanol+60.75% THF ("CHX-CHA-AgSD-L");

2% CHX+1.5% CHA+0.75% AgSD+1% 1,2 Decanediol+1% Lactic acid+3% 93A PU+1% 60D PU+30% Methanol+59.75% THF ("CHX-CHA-AgSD-L-D");

2% CHX+1.5% CHA+0.75% AgSD+1% 1,12 Dodecanediol+1% Lactic acid+3% 93A PU+1% 60D PU+30% Methanol+59.75% THF ("CHX-CHA-AgSD-L-1,2 Dod");

2% CHX+1.5% CHA+0.75% AgSD+1% 1,12 Dodecanediol+1% Lactic acid+3% 93A PU+1% 60D PU+30% Methanol+59.75% THF ("CHX-CHA-AgSD-L-1,12 Dod");

2% CHX+1.5% CHA+0.75% AgSD+1% 1,2 Tetradecanediol+1% Lactic acid+3% 93A PU+1% 60D PU+30% Methanol+59.75% THF ("CHX-CHA-AgSD-L-1,14 TD");

2% CHX+1.5% CHA+0.75% AgSD+1% 1,2 Octanediol+1% Lactic acid+3% 93A PU+1% 60D PU+30% Methanol+59.75% THF ("CHX-CHA-AgSD-L-O");

3.5% CHX+0.75% AgSD+1% 1,2 Octanediol+1% Lactic acid+3% 93A PU+1% 60D PU+30% Methanol+59.75% THF ("CHX-AgSD-L-O"); and 3.5% CHA+0.75% AgSD+1% 1,2 Octanediol+1% Lactic acid+3% 93A PU+1% 60D PU+30% Methanol+59.75% THF ("CHA-AgSD-L-O").

In specific, non-limiting examples, the present invention provides for the following impregnation solutions, which may be used, not by way of limitation, for the impregnation of soft tissue patches (e.g., polytetrafluoroethylene ("PTFE") soft tissue patches ("STPs"), and also provides for medical articles, such as STPs (e.g. PTFE STPs) impregnated therewith:

0.1% Silver carbonate+0.2% CHX+0.15% CA+1% 0 ("S-CHX-CHA-O"); 0.1% Silver carbonate+0.2% CHX+0.15% CHA+1% D ("S1-CHX-CHAD"); and 0.05% Silver carbonate+0.2% CHX+0.15% CHA+1% D (S2-CHX-CHA-D), where S=Silver carbonate, D=1,2 Decanediol, and 0=1,2 Octanediol.

In specific, non-limiting embodiments, the present invention provides for the following impregnation solutions which may be applied to silicone articles, e.g., urinary catheters, for example but not limited to as part of a two-step method, and also provides for medical articles, such as catheters, e.g. urinary catheters, e.g. silicone urinary catheters, impregnated therewith:

CHX-O: 2% (w/v) CHX+1% O+15% (w/v) Silastic Medical Adhesive Type A+1% glycerin+81% (v/v) THF;

CHX-D: 2% (w/v) CHX+1% D+15% (w/v) Silastic Medical Adhesive Type A+1% glycerin+81% (v/v) THF;

CHX-1,2Dod: 2% (w/v) CHX+1% 1,2 Dodecandiol+15% (w/v) Silastic Medical Adhesive Type A+1% glycerin+81% (v/v) THF;

CHX-1,12Dod: 2% (w/v) CHX+1% 1,12 Dodecanediol+15% (w/v) Silastic Medical Adhesive Type A+1% glycerin+81% (v/v) THF; OR CHX-TD: 2% (w/v) CHX+1% TD+15% (w/v) Silastic Medical Adhesive Type A+1% glycerin+81% (v/v) THF In specific, non-limiting embodiments, the present invention provides for the following impregnation solutions which may be applied to wound coatings, and also provides for wound coverings impregnated therewith:

| Ingredients | (% w/w) |
|---|---|
| Antimicrobial composition 1 | |
| CHA | 0.15 |
| CHX | 0.15 |
| AgSD | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |
| Antimicrobial composition 2 | |
| CHA | 0.15 |
| CHX | 0.15 |
| AgSD | 0.30 |
| Lactic Acid | 0.50 |
| 1,12 Dodecanediol | 0.50 |
| Polyurethane 93A | 0.40 |
| Polyurethane 60D | 0.10 |
| Methanol | 30.00 |
| Tetrahydrofuran | 67.90 |
| Antimicrobial composition 3 | |
| CHA | 0.15 |
| CHX | 0.15 |
| Silver Carbonate | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |
| Antimicrobial composition 4 | |
| Polyhexamethylene biguanide | 0.30 |
| Silver Carbonate | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 67.90 |
| Antimicrobial composition 5 | |
| CHA | 0.15 |
| CHX | 0.15 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |
| Antimicrobial composition 6 | |
| Polyhexamethylene biguanide | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |

In a particular, non-limiting set of embodiments, a composition described in this section may be comprised in a wipe or a wound dressing.

4.5 Methods for Producing a Bio-Film Resistant Surface

The present invention provides for methods of producing a bio-film resistant surface, comprising exposing the surface to a composition comprising a biguanide, an alkanediol, and a solvent, where the biguanide is present at between about 0.1 and 5 percent (weight/volume), or between about 2.5 and 4 percent (weight/volume) (where the article is to be "dipped" in the composition for a period of between about 5 seconds and 5 minutes or between about 5 seconds and 1 minute) or between about 0.5 and 3 percent (weight/volume), and the alkanediol is present at between about 0.5 and 5 percent (volume/volume) (Note that octanediol, for example, is a waxy solid but may be melted prior to adding to the solvent), and the solvent is selected from the group consisting of an alcohol (e.g. methanol, ethanol, isopropanol, and mixtures thereof), tetrahydrofuran and mixtures thereof. In preferred non-limiting embodiments of the invention, the biguanide is chlorhexidine, such as chlorhexidine free base, chlorhexidine diacetate, chlorhexidine gluconate, or a mixture thereof, and the alkanediol is octanediol. Such compositions may further comprise one or more additional antimicrobial agent (in an amount between about 0.05 and 3 percent, preferably between about 0.2 and 1.5 percent (weight/volume), one or more hydroxy acid (in an amount between about 0.5 and 3 percent, preferably between about 0.2 and 2 percent (volume/volume), and/or one or more polymer (in an amount between about 1 and 20 percent or between 1 and 30 percent or between about 1 and 10 percent, or between about 3 and 6 percent (weight/volume). In preferred non-limiting embodiments, the additional antimicrobial agent may be a silver compound, such as, but not limited to, silver sulfadiazine, the hydroxy acid may be lactic acid, and/or the polymer may be 93A polyurethane, 60D polyurethane, silastic medical adhesive type A, or a mixture thereof.

The surface may be exposed to the composition by immersing the surface in the composition or by applying the composition to the surface, for example by a spray, a stream, or a wipe.

In non-limiting embodiments of the invention, the composition may be exposed to the surface for a period of time such that the biguanide impregnates the surface.

In non-limiting embodiments of the invention, the composition may be exposed to the surface for a period of time such that the physical properties of the surface are altered, for example, where there is swelling of the surface; Such alteration should not be such that the surface is damaged with regard to its intended use.

For example, where the surface is a surface of a catheter fabricated from a polymer, the catheter may be immersed in the composition and/or the composition may be introduced into the interior of the catheter. In one non-limiting embodiment, the ends of the catheter are sealed to prevent entry of the composition into the lumen. In another non-limiting embodiment, the composition is introduced into the interior of the catheter. In another non-limiting embodiment, the catheter may be briefly dipped into the composition. In non-limiting embodiments, a catheter surface is exposed to the composition for a period of between about 5 seconds and 5 hours, or between about 1 minute and 2 hours, or between about 5 seconds and 5 minutes, or between about 5 seconds and 1 minute.

In one particular set of embodiments, the present invention provides for a two-step method for providing a bio-film resistant surface. In the first step, an additional antimicrobial agent as set forth above, (for example, but not limited to, triclosan or a silver compound such as silver sulfadiazine), may be applied as a first solution comprising the antimicrobial agent at a concentration between about 0.05 and 3 percent (weight/volume), said solution optionally further comprising a hydroxy acid at a concentration between about 0.5 and 3 percent (volume/volume), in a solvent selected from the group consisting of an alcohol (e.g. methanol, ethanol, isopropanol, and mixtures thereof), tetrahydrofuran and mixtures thereof (preferably methanol). Biguanide, alkanediol, polymer and optionally hydroxy acid are applied in the second step, comprised in a solution wherein biguanide is present at between about 0.1 and 5 percent (weight/volume), or between about 0.5 and 3 percent (weight/volume), alkanediol is present at between about 0.5 and 5 percent (volume/volume), polymer is present at a concentration between about 1 and 20 percent or between about 1 and 10 percent or between about 3 and 6 percent (weight/weight) and the solvent is selected from the group consisting of an alcohol (e.g. methanol, ethanol, isopropanol, and mixtures thereof), tetrahydrofuran and mixtures thereof; hydroxy acid, where present, is in an amount of between about 0.5 and 3 percent (volume/volume). In each step, soaking may be for time intervals between about 5 seconds and 5 hours, or between about 1 minute and 2 hours, or between about 5 seconds and 5 minutes, or between about 5 seconds and 1 minute.

In a specific, non-limiting embodiment of the two-step method, in the first step, a solution containing about 30 percent THF (volume/volume), about 65 percent methanol (volume/volume), about 3 percent triclosan (TC) (weight/volume), and about 2 percent lactic acid (L) (volume/volume), may be used, into which a polyurethane catheter may be dipped for a time period of at least about 30 seconds or at least about one minute, and then allowed to dry, for example (but not by way of limitation) 48 hours (or however long drying requires). For the second step, a solution may be prepared containing about 30 percent methanol (volume/volume), about 63 percent THF (volume/volume), about 2 percent octanediol (O) (volume/volume), about 1 percent lactic acid (L)(volume/volume), about 4 percent chlorhexidine free base (CHX)(weight/volume), about 4 percent 93A polyurethane (weight/volume), and about 1 percent 60D polyurethane (weight/volume). (The polyurethanes may be first dissolved in THF and the other components may be dissolved in methanol and then the two resulting solutions may be mixed). The catheter resulting from the first step may be dipped into this solution for at least about 5 seconds, and then allowed to dry.

In another specific, non-limiting embodiment of the two-step method, in step 1, a silicone article (e.g. a catheter) or portion thereof may be soaked for 1 hour in a solution comprising about 0.3 percent triclosan (weight/volume) and about 1.0 percent lactic acid (volume/volume) in about 30 percent methanol (volume/volume)/about 67 percent THF (volume/volume). The catheter may be removed, dried, rinsed in water and dried again. In step 2, the catheter resulting from step 1 may be dipped in a solution comprising about 2 percent chlorhexidine free base (weight/volume), about 10 percent Silastic Medical Adhesive Type A (weight/volume), about 2 percent octanediol (volume/volume) and about 88 percent THF (volume/volume) (where THF is used to bring the volume to 100 percent) and dried.

In yet further specific non-limiting examples of the invention, silicone catheters, for example urinary catheters, may be impregnated by a two-step method as follows. Step 1: Catheters may be soaked for 1 hour in 0.3% Triclosan (T) (w/v)+1.0% L (Lactic Acid) (v/v) in 30% Methanol (v/v)+68.7% (v/v) THF. The catheters may be removed, dried for 1 hour, rinsed in water and dried for another hour. Step 2: Catheters may be dipped in the following solutions and dried for 24 hours and then used for testing:

CHX-O: 2% (w/v) CHX+1% O+15% (w/v) Silastic Medical Adhesive Type A+1% glycerin+81% (v/v) THF;

CHX-D: 2% (w/v) CHX+1% D+15% (w/v) Silastic Medical Adhesive Type A+1% glycerin+81% (v/v) THF;

CHX-1,2Dod: 2% (w/v) CHX+1% 1,2 Dodecandiol+15% (w/v) Silastic Medical Adhesive Type A+1% glycerin+81% (v/v) THF;

CHX-1,12Dod: 2% (w/v) CHX+1% 1,12 Dodecanediol+15% (w/v) Silastic Medical Adhesive Type A+1% glycerin+81% (v/v) THF; OR CHX-TD: 2% (w/v) CHX+1% TD+15% (w/v) Silastic Medical Adhesive Type A+1% glycerin+81% (v/v) THF.

4.6 Articles Having a Bio-Film Resistant Surface

The present invention provides for an article having at least one surface which is rendered bio-film resistant using the compositions and methods set forth above.

In non-limiting embodiments, the present invention provides for an article having at least one surface comprising, as active agents, a biguanide (e.g. chlorhexidine free base or a chlorhexidine salt) at between about 250 and 5000 $\mu g/cm^2$ of surface or between about 500 and 1000 $\mu g/cm^2$ of surface and an alkanediol (e.g. octanediol) at between about 200 and 1500 $\mu g/cm^2$ of surface, and optionally a hydroxy acid (e.g. lactic acid) at between about 100 and 800 $\mu g/cm^2$ of surface, and/or optionally a silver compound (e.g. AgSD) at between about 0-200 $\mu g/cm^2$ of surface.

Medical articles that may be treated according to the invention are either fabricated from or coated or treated with biomedical polymer and include, but are not limited to, catheters including urinary catheters and vascular catheters (e.g. peripheral and central vascular arterial and venous catheters), wound drainage tubes, arterial grafts, soft tissue patches, gloves, shunts, stents, tracheal catheters, wound dressings, bandages, drapes, intrauterine devices, intravaginal devices, sutures, staples, guide wires and prosthetic devices (e.g. heart valves and LVADs). Vascular catheters that may be prepared according to the present invention include, but are not limited to, single and multiple lumen central venous catheters, peripherally inserted central venous catheters, emergency infusion catheters, percutaneous sheath introducer systems and thermodilution catheters, including the hubs and ports of such vascular catheters.

In non-limiting embodiments, articles made of substrates such as polyurethane, silicone rubber, natural rubber latex, polyvinyl chloride, as well as cotton, silk (wound dressings) can be treated with a composition of the invention.

Below are a series of working examples. The compositions, methods and articles described in the below working examples are hereby incorporated into this detailed description.

5. EXAMPLE 1

Effect on Zone of Inhibition

Polyurethane (PU) 7 Fr. central venous catheters (CVC) were treated with octanediol ("O"), lactic acid ("L") and chlorhexidine ("C")-containing solutions, in the presence or absence of other active agent.

Preparation of Coating Solution.

Two separate solutions were prepared, Solution A and Solution B, as follows:

Solution A: Chlorhexidine, octanediol, with or without lactic acid, in methanol; and Solution B: 93A polyurethane and 60D polyurethane in THF, and then the two solutions were mixed thoroughly prior to treatment. The amounts of active agents are set forth in Table 1, below, and the amount of polymer in the final solution, which was about 65 percent THF (volume/volume ("v/v")) and about 30 percent methanol (v/v) was 4 percent (weight/volume ("w/v")) 93A polyurethane and 1 percent (w/v) 60D polyurethane.

Impregnation of Catheters.

Catheters (6 cm in length, both ends sealed) were dipped in coating solutions prepared as above, containing active ingredients as indicated in Table 1. The catheters were dipped for 5 seconds in the solution and dried at room temperature for 24 hours and then used for testing.

TABLE 1

| Group | Composition |
|---|---|
| 1) | 4% CHX |
| 2) | 4% CHX + 3% L |
| 3) | 4% CHX + 3% O |
| 4) | 4% CHX + 2% O + 1% L |
| 5) | 3% CHX + 1% TC |
| 6) | 3% CHX + 1% TC + 2% O + 1% L |
| 7) | 3% CHX + 1% AgSD |
| 8) | 3% CHX + 1% AgSD + 2% O + 1% L |

NOTE:
CHX = Chlorhexidine free base

Zone of Inhibition (ZOI) Test.

Three 0.5 cm segments of each group of catheters, prepared as described above, were embedded vertically in modified trypticase soy agar (TSA) media seeded on the surface with 0.3 ml of $10^8$ colony forming units (CFU) per ml of bacteria or 105 cfu/ml of yeast and the plates were incubated at 37° C. for 24 hours. The diameters of zones of inhibition of bacterial growth around the catheter segments were measured. The results are presented in Table 2.

TABLE 2

| | | Zone of Inhibition (mm) | | |
|---|---|---|---|---|
| Group | Active Agents | P. aeruginosa | S. aureus | C. albicans |
| 1) | 4% CHX | 11.0 | 13.0 | 12.0 |
| 2) | 4% CHX + 3% O | 11.5 | 13.0 | 12.0 |
| 3) | 4% CHX + 3% L | 11.0 | 13.0 | 12.0 |
| 4) | 4% CHX + 2% O + 1% L | 11.0 | 13.5 | 12.0 |
| 5) | 3% CHX + 1% TC* | 9.5 | 14.0 | 12.0 |
| 6) | 3% CHX + 1% TC + 2% O + 1% L | 11.0 | 15.0 | 12.0 |
| 7) | 3% CHX + 1% AgSD | 9.5 | 12.0 | 11.0 |
| 8) | 3% CHX + 1% AgSD + 2% O + 1% L | 11.5 | 13.5 | 13.0 |
| 9) | 5% O + 3% L | 0 | 8.0 | 0 |

*TC is triclosan.
Conclusion: The zone-inhibiting activity was not significantly different between the group containing O + L and the group without O + L.

6. EXAMPLE 2

Effect on Microorganism Adherence

Bacterial adherence on Polyurethane (PU) 7 Fr. (white) central venous catheters (CVC) treated with O+L+C and other antiseptics, as set forth in the preceding section, was evaluated using an in vitro agar track model.

Agar Tract Model.

The medium used was 0.5% agar (w/v) 20% bovine adult serum (BAS) (v/v)+0.5% milk (v/v)+0.03% trypticase soy broth medium powder (TSB) (w/v) in phosphate buffered saline (PBS). First, agar and TSB was dissolved in PBS, and a magnetic stirring rod was included in the flask. The medium was sterilized by autoclaving at 121° C. for 20 min. After autoclaving, it was allowed to cool down to 45-48° C. in a water bath put on a magnetic stirrer. Then, BAS and milk were warmed to room temperature, and 5 ml of milk were mixed with 5 ml BAS in a sterile culture tube and added to the agar/TSB-containing flask with gentle stirring. Then the remaining amount of BAS was added to the flask. The medium was maintained at 45-48° C. 12.5 ml aliquots of medium were dispensed into different culture tubes and allowed to solidify at room temperature.

Evaluation of Bacterial Adherence.

Catheter segments, 4 cm long and sealed at both ends, were inserted vertically into the center of the medium in each tube with 0.5 cm of the catheter protruding out of the medium. The caps of each tube were sealed with parafilm to prevent dessication. 5 catheter segments were used for each test. Untreated catheter segments were used as the control.

After 30 minutes, each catheter segment was lifted up (approximately 0.5 cm) and 25 µl of the culture (1-3×$10^8$ cfu/ml of P. aeruginosa or 1-3×$10^6$ cfu/ml C. albicans) was added on the catheter just near the surface of the medium so that the inoculum was also spread on medium surface. The catheter was then placed back to its original position and incubated at 37° C. for 7 days.

Then, the catheter segments were removed from the tubes and blotted on tissue. They were rinsed twice in 10 ml saline (6 segments/10 ml saline) and blotted dry. 0.5 cm was then cut off from both the ends of each catheter segment. Each catheter segment was then put in 4 ml LTSB (drug inactivating medium) in a culture tube and sonicated for 20 min. 0.5 ml aliquot from each tube was then plated out on TSA plates and incubated for 24-48 h. The results are shown in Table 3 (adherence of P. aeruginosa) and Table 4 (adherence of C. albicans).

TABLE 3

P. aeruginosa adherence (infected 30 minutes after implantation)

| | | Adherence of P. aeruginosa | |
|---|---|---|---|
| Group | Active agents | CFU/cm | Log10 Reduction from control counts |
| Control | (uncoated) | $1.1 \times 10^4$ | — |
| 1) | 4% CHX | $1.8 \times 10^3$ | 0.78 |
| 2) | 4% CHX + 3% L | $8.3 \times 10^2$ | 1.14 |
| 3) | 4% CHX + 3% O | $1.8 \times 10^2$ | 1.78 |
| 4) | 4% CHX + 2% O + 1% L | 92 | 2.08 |
| 5) | 3% CHX + 1% TC | $8.9 \times 10^2$ | 1.04 |
| 6) | 3% CHX + 1% TC + 2% O + 1% L | $1.1 \times 10^2$ | 2.0 |
| 7) | 3% CHX + 1% AgSD | $5.8 \times 10^2$ | 1.28 |
| 8) | 3% CHX + 1% AgSD + 2% O + 1% L | 4 | 3.44 |
| 9) | 3% O + 3% L | $9 \times 10^3$ | 0.1 |

TABLE 4

C. albicans adherence (infected 30 minutes after implantation)

| | | Adherence of C. albicans | |
|---|---|---|---|
| Group | Active agents | CFU/cm | Log10 Reduction from control counts |
| Control | (uncoated) | $2.9 \times 10^3$ | — |
| 1) | 4% CHX | $1.0 \times 10^3$ | 0.5 |
| 2) | 4% CHX + 3% L | $1.1 \times 10^3$ | 0.46 |
| 3) | 4% CHX + 3% O | $1.9 \times 10^2$ | 1.2 |
| 4) | 4% CHX + 2% O + 1% L | 4 | 2.9 |
| 5) | 3% CHX + 1% TC | 90 | 1.5 |
| 6) | 3% CHX + 1% TC + 2% O + 1% L | 0 | 3.5 |
| 7) | 3% CHX + 1% AgSD | 44 | 1.9 |
| 8) | 3% CHX + 1% AgSD + 2% O + 1% L | 0 | 3.5 |

CONCLUSIONS

As regards *P. aeruginosa* adherence, catheters having surfaces treated with C+O and C+O+L showed lower adherence. Of all the groups C and AgSD with O and L had significantly lower adherence. This result indicates that biofilm formation and bacterial adherence on medical devices can be significantly reduced by treating the device with an antimicrobial solution containing C+O+L.

As regards *C. albicans* adherence, the group of catheters having surfaces treated with 0 and L showed significantly lower adherence.

7. EXAMPLE 3

Two-Step Coating Method

In the preceding sections, catheters were coated with CHX+T+O+L along with a polymer by a dip method. With dipping, the percent of CHX in the solution is preferably in the range of 2.5-4%, for the catheter to be effective especially against *P. aeruginosa* (ZOI more than 10 mm) and *C. albicans* (ZOI more than 13 mm). For long term efficacy against *S. aureus*, a ZOI greater than 15 mm is most preferred. The catheters coated by the one step dipping method show effective ZOI against *P. aeruginosa* and *C. albicans*. However the ZOI against *S. aureus* is about 15 mm when CHX+Triclosan is 3%+1% (w/v) in the coating solution. Increasing the Triclosan in the coating solution can increase the efficacy against *S. aureus*. However, Triclosan has essentially no activity against *P. aeruginosa*. Furthermore, coating catheters with solutions containing higher concentrations of Triclosan may lower the amount of CHX uptake by the catheter (since the ratio of CHX to Triclosan will be lower) which results in lower efficacy against *P. aeruginosa*.

In order to provide a catheter which is effective, for extended periods, against *P. aeruginosa*, *C. albicans* and *S. aureus*, a two step method was developed by which higher concentrations of both triclosan and chlorhexidine could be incorporated along with octanediol and lactic acid.

According to the two-step method, triclosan and lactic acid is applied to the surface in the first step, and chlorhexidine, octanediol, lactic acid and polymer is applied in the second step.

For the first step, a solution containing about 30 percent THF (v/v), about 65 percent methanol (v/v), about 3 percent triclosan (TC) (w/v), and about 2 percent lactic acid (L) (v/v), was prepared. For example, for each about 100 ml of solution to be prepared, 30 ml THF, 65 ml Methanol, 3 g Triclosan, and 2 ml Lactic acid are mixed. A portion of a polyurethane 7 fr. blue catheter, with the top end sealed to prevent entry of liquid into the catheter, was soaked in this solution for 1 minute and then allowed to dry for 48 hours.

For the second step, a solution was prepared containing about 30 percent methanol (v/v), about 63 percent THF (v/v), about 2 percent octanediol (O) (v/v), about 1 percent lactic acid (L)(v/v), about 4 percent chlorhexidine free base (CHX) (w/v), about 4 percent 93A polyurethane (w/v), and about 1 percent 60D polyurethane (w/v). This solution was first prepared by dissolving the chlorhexidine, lactic acid and octanediol in the methanol, dissolving the polyurethanes in the THF, and then mixing the solutions together. For example, for each about 100 ml of solution to be prepared, 2 ml octanediol, 1 ml lactic acid, and 4 mg chlorhexidine are dissolved in 30 ml methanol, and 4 g 93A polyurethane and 1 g 60D polyurethane are dissolved in 63 ml THF, and then the methanol and THF solutions are mixed. Then, the catheter from Step 1 was dipped into this solution for 5 seconds and dried at room temperature overnight.

Control (uncoated) catheters, catheters treated by a one-step method, or by the two-step method described above, were prepared, as follows:
1) Control (uncoated catheter)
2) Catheter by 2 steps (Step 1 3% T+2% L) and Step 2 (4% CHX+1% L+2% O)
3) Catheter by 1 step (3% CHX+1.0% T+2% O+1% L)

The zones of inhibition for each of these catheters were then determined, using methods as set forth in Example 1, above. The results are presented in Table 5.

TABLE 5

| | Zone of Inhibition (mm) | | |
|---|---|---|---|
| Group | P. aeruginosa | S. aureus | C. albicans |
| 1 (control) | 0 | 0 | 0 |
| 2 (2-step) | 12.5 | 17.0 | 14.5 |
| 3 (1-step) | 11.0 | 15.0 | 12.0 |

Conclusion: The two-step method produced a catheter which showed higher activity against all the organisms tested.

Bacterial adherence to the three catheters tested above was also determined, using methods described in Example 2. The results are shown in Table 6.

TABLE 6

| Group | P. aeruginosa adherence (cfu/cm) |
|---|---|
| 1 (control) | $6.4 \times 10^3$ |
| 2 (2-step) | $1.7 \times 10^2$ |
| 3 (1 step) | $1.0 \times 10^3$ |

Conclusion Catheters prepared by the two-step method showed lower adherence of *P. aeruginosa*.

8. EXAMPLE 4

Further Bacterial Adherence Studies

Further studies evaluated bacterial adherence on polyurethane (PU) 4 Fr. peripherally inserted central venous catheters treated with O+L+C and other antiseptics using an in vitro agar tract model. Preparation of catheters, and the agar tract model, were as described in Examples 1 and 2 above, respectively. The results are shown in Table 7.

TABLE 7

P. aeruginosa adherence (infected 30 minutes after implantation)

| Group | Adherence of P. aeruginosa (cfu/cm) |
|---|---|
| Control (uncoated catheters) | $1 \times 10^3$ |
| 2.5% CHX + 1% TC | 96 |
| 2.5% CHX + 1% TC + 2% L | 92 |
| 2.5% CHX + 1% TC + 3% O | 23 |
| 2.5% CHX + 1% TC + 2% O + 1% L | 0 |

Conclusion: Catheters treated with C + O and C + O + L showed significantly lower adherence.

9. EXAMPLE 5

Catheters Treated with Two Forms of Chlorhexidine

Studies were performed to evaluate adherence of *P. aeruginosa* on catheters treated with solutions containing chlorhexidine acetate (CHA)+chlorhexidine free base (CHX) The method of coating and testing of adherence were the same as described in Examples 1 and 2 above, respectively. The results are shown in Table 8.

TABLE 8

P. aeruginosa adherence (infected 30 minutes after implantation)

| Group | Adherence of P. aeruginosa (cfu/cm) |
|---|---|
| Control (uncoated catheters) | $3.1 \times 10^3$ |
| 2% CHA + 1.5% CHX | $3.7 \times 10^2$ |
| 2% CHA + 1.5% CHX + 3% O | 58 |
| 2% CHA + 1.5% CHX + 0.5% TC | $1 \times 10^2$ |
| 2% CHA + 1.5% CHX + 0.5% TC + 3% O | 23 |

Conclusion: Catheters Coated with solutions containing CHA + CHX + O or with CHA + CHX + T C + O showed significantly lower adherence.

10. EXAMPLE 6

Comparison of Octoxyglycerine and Octanediol

Studies were performed to evaluate adherence of *P. aeruginosa* on central venous catheters (CVC) impregnated with chlorhexidine, with or without either octoxyglycerine ("OCG") or octanediol. The catheters were prepared essentially as described in Example 1 and adherence was measured using the agar tract model as set forth in Example 2. Results, measured 7 days post-infection, are shown in Table 9.

TABLE 9

P. aeruginosa adherence (infected 30 minutes after implantation)

| Group | (cfu/cm) |
|---|---|
| Control (uncoated catheters) | $4.1 \times 10^3$ |
| 3% CHX | $3.8 \times 10^2$ |
| 3% CHX + 3% O | 8 |
| 3% CHX + 3% OCG | $1 \times 10^2$ |

Conclusion The adherence was significantly lower in the Octanediol group 7 days post infection. Without being bound by any particular theory, it is believed these results may be caused by octoxyglycerin, which is viscous fluid, remaining on the surface of the catheter as an oily coating which has diffused into the agar by the 7th day. In contrast, octanediol, which is a waxy powder, remains on the catheter surface and does not diffuse into the agar, so that bacteria which comes in contact with the surface of an octanediol coated catheter gets killed.

11. EXAMPLE 7

Evaluation of S. aureus Adherence

Studies were performed to evaluate adherence of *S. aureus* to polyurethane (PU) 4 Fr. central venous catheters (CVC) treated with C+T+O+L (prepared as in Example 1), using an in vitro agar track model (as described below).

Catheter segments, 4 cm long and sealed at both ends, were inserted vertically into the center of medium in each tube with 0.5 cm of the catheter protruding out of the medium (as in Example 2). The caps of each tube were sealed with parafilm to prevent dessication. 5 catheter segments were used for each test. Untreated catheter segments were used as the control.

After 21 days, the catheters were transferred to fresh agar tracts and after 30 minutes each catheter segment was lifted up (approximately 0.5 cm) and 25 ul of the culture ($1-3 \times 10^8$ cfu/ml of *S. aureus*) was added on the catheter just near the surface of the medium so that the inoculum was also spread on medium surface. The catheter was then placed back into its original position and incubated at 37° C. for 7 days The catheter segments were removed from the tubes and blotted on tissue. They were rinsed twice in 10 ml saline (6 segments/10 ml saline) and blotted dry. 0.5 cm was then cut off from both the ends of each catheter segment. Each catheter segment was then put in 4 ml LTSB (drug inactivating medium) in a culture tube and sonicated for 20 min. 0.5 ml aliquot from each tube was then plated out on TSA plates and incubated for 24-48 h. The results are shown in Table 10.

TABLE 10

S. aureus adherence (infected 21 day post implantation)

| Group | Adherence of S. aureus (cfu/cm) |
|---|---|
| Control (uncoated catheters) | $1.0 \times 10^4$ |
| 2.5% CHX + 1% TC | $2.8 \times 10^2$ |
| 2.5% CHX + 1% TC + 2% O + 1% L | 0 |

Conclusion: Group containing O + L showed no adherence even after infected 21 days post implantation.

12. EXAMPLE 8

Treated Silicone Catheters

Studies were performed to evaluate the antimicrobial efficacy of silicone urinary catheters impregnated with chlorhexidine, triclosan, octanediol and lactic acid.

One set of catheter portions was treated by a one-step method, as follows.

Catheters were soaked in solutions comprising active agents dissolved in about 60 percent THF (v/v)+about 30 percent methanol (v/v) and the total volume was made up to 100% with THF. The catheters were soaked for 1 hour, dried at room temperature for 1 hour, rinsed in water and then dried for another hour and used for testing.

Another set of catheter portions was treated by a two-step method, as follows. In step 1, portions of silicone urinary catheters were soaked for 1 hour in 0.3% TC (w/v)+1.0% L (v/v) in 30% Methanol (v/v)+67% (v/v) THF. The catheters were removed, dried for 1 hour, rinsed in water and dried for another hour. In step 2, catheters were dipped in 2% CHX (w/v)+2% 0 (v/v)+10% (w/v) Silastic Medical Adhesive Type A THF (THF used to bring the volume to 100%) and air dried at room temperature for 24 hours and then used for testing.

Bacterial adherence was evaluated using an in vitro urinary tract model, as follows. The model consists of two tubes one of which was an open cylindrical tube with one end capped and the other end sealed with a rubber cork with a hole in the center (Tube 1). The tube was crimped from both the sides at the center. The second tube was open at one end and was used for collection of urine (Tube 2). Both the tubes were sterilized with ethylene dioxide. Catheter segments of 6 cm in length, with both the ends sealed with silicone to prevent intraluminal contamination with bacteria, were sterilized and were inserted from top end of Tube 1 after lifting the cap aseptically and placed in the hole of the rubber cork at the end.

The sterile modified Trypticase Soya Agar was cooled to 40° C. and then poured along the sides of the tube around the catheter leaving the upper 1 cm of the catheter protruding out in the space above the agar tract, which represented the bladder. When the medium solidified in the tube, the cork at the bottom of the tube was removed gently without disturbing the agar column on the top thus exposing the lower end of the catheter. This lower end of the agar column with the catheter protruding represented the meatus and the agar surrounding the catheter simulated the urethra. This tube was then fixed on "Tube 2" to collect small amount of urine that flowed down the agar tract.

The "meatus" was inoculated daily with 20 µl of $10^6$ cfu/ml of C. albicans after dismantling the collection tube (Tube 2). The "bladder" was filled daily with fresh sterile urine. The "bladder" and the "meatus" were cultured daily on TSA to determine the presence of bacterial growth. On the day a positive "bladder" culture was found, the catheter segment was also processed for determination of bacterial colonization on the catheter surface. This was done by removing the catheter segment from the "bladder" end of the model, rinsing with saline and rolling it on a D/E agar plate followed by incubation for 24 hours at 37° C. to semi-quantitatively determine the bacterial growth on the surface of the catheter.

The results are shown in Table 11.

TABLE 11

| | Duration of activity against C. albicans for | |
|---|---|---|
| | 1-step vs 2-step Preparation Method (Days) | |
| Active agents | 1-step | 2-step |
| Control | 1 | 1 |
| 2% CHX + 0.3% TC | 3 | 8 |
| 2% CHX + 0.3% TC + 1.% L + 2% O | 10 | 30 |

Conclusion: Silicone urinary catheters treated with C + TC + O + L showed longer activity. Catheters prepared by the two step method where the CHX was coated on the outer surface along with a silicone matrix showed superior activity. The two-step method was found to be better for releasing CHX from silicone rubber catheters. Incorporation of chlorhexidine on the outer coating of the silicone matrix appears to release an effective amount of chlorhexidine.

13. EXAMPLE 9

Treatment of PTFE Patches

Studies were performed to evaluate the antimicrobial effect of surface treatment of polytetrafluoroethylene ("PTFE") soft tissue patches. In particular, such patches were impregnated with CHX+Silver Carbonate (AgC) and CHX+AgC+O+L.

1 $cm^2$ pieces were soaked in solutions comprising about 60 percent THF (v/v), about 20 percent Methanol (v/v) and about 20 percent ammonium hydroxide (v/v) as well as the active agents indicated below, then suctioned using a vacuum pump and left for 5 minutes. The pieces were removed, dried and rinsed in water. After 24 hours the patches were tested.

The following Adherence Testing Method was used. 4 pieces of PTFE tissue patch, each 1 $cm^2$, were soaked in medium containing 50% TSB+50% BAS (v/v) (1 ml per 1 $cm^2$ of each piece) and placed on an orbital shaker at 37° C. for 7 days. The pieces were removed, and transferred to a fresh media containing 105 cfu of S. aureus/ml (1 ml/1 $cm^2$) and incubated for 24 hours at 37° C. The pieces were removed and rinsed twice in (2 ml/1 $cm^2$) saline) by vortexing at low speed, blotted dry and suspended in drug inactivating media (4 ml/1 piece) and sonicated. 0.5 ml. aliqouts were plated. The results are shown in Table 12.

TABLE 12

| Group | Adherence (Cfu/$cm^2$) |
|---|---|
| Control (untreated Patch) | >105 |
| 0.3% CHX + 0.1% AgC | 66 |
| 0.3% CHX + 0.1% AgC + 1% L + 2% + O | 5 |

Conclusion: The Group containing O + L showed lower adherence.

14. EXAMPLE 10

Agents at Catheter Surface

Pre-weighed 7 Fr catheters having an outer diameter measured to be 0.092" or 0.234 cm diameter were dipped in coating solution comprising 1) 4% CHX+2% Octanediol+1% Lactic acid, in about 30% methanol, about 63% THF and 2) 3.5% CHX+0.75% AgSD+2% Octanediol+1% Lactic acid in about 30% methanol, about 62.75% THF.

The catheters were dipped and immediately wrapped in pre-weighed aluminum foil to prevent any solvent evaporation and the weight of the coating solution on the catheter was determined.

The coating weights were found to be:
1) 0.022 grams total coating per $cm^2$
2) 0.021 grams total coating per $cm^2$ Based on these weights and the percentages of active agents present, the following amounts of active agents were calculated to be present:

(1) LA=1%=>220 micrograms/$cm^2$ Surface
  CHX=4%=>880 micrograms/$cm^2$ Surface
  1,2-Octanediol=2%=>440 micrograms/$cm^2$ Surface
(2) LA=1%=>210 micrograms/$cm^2$ Surface
  CHX=3.5%=>735 micrograms/$cm^2$ Surface
  1,2-Octanediol=2%=>420 micrograms/$cm^2$ Surface
  AgSD=0.75%=>158 micrograms/$cm^2$ Surface

15. EXAMPLE 11

Zones of Inhibition

Zones of inhibition associated with catheters treated with the active agents indicated in Table 13 were measured. The methods of preparing the catheters and for measuring zones of inhibition were essentially as set forth in Example 1 (for the particular combinations of active agents tested).

TABLE 13

| Active Agents | Zone of Inhibition (mm) | | |
|---|---|---|---|
| | P. aeruginosa | S. aureus | C. albicans |
| 3.5% CHX + 2% O + 1% L | 11.0 | 12.5 | 11.5. |
| 3.5% CHX + 2% O + 1% Salicylic acid | 11.0 | 13.0 | 13.5. |
| 3.5% CHX + 2% OCG + 1% L | 11.0 | 12.5 | 11.5 |
| 3.5% CHX + 1% O + 1% OCG + 1% L | 11.5 | 13.0 | 13.0 |

Conclusion: The activity of catheters with O + OCG was slightly higher than that with O or OCG alone against C. albicans.

16. EXAMPLE 12

Bacterial Adherence to Impregnated Catheters

Polyurethane catheter segments were impregnated with the following solutions.
1) 2% CHX+1.5% CHA+0.75% AgSD+1% Lactic acid+3% 93A PU+1% 60D PU+30% Methanol+60.75% THF (CHX-CHA-AgSD-L)
2) 2% CHX+1.5% CHA+0.75% AgSD+1% 1,2 Decanediol+1% Lactic acid+3% 93A PU+1% 60D PU+30% Methanol+59.75% THF (CHX-CHA-AgSD-L-D)
3) 2% CHX+1.5% CHA+0.75% AgSD+1% 1,12 Dodecanediol+1% Lactic acid+3% 93A PU+1% 60D PU+30% Methanol+59.75% THF (CHX-CHA-AgSD-L-1,2 Dod)
4) 2% CHX+1.5% CHA+0.75% AgSD+1% 1,12 Dodecanediol+1% Lactic acid+3% 93A PU+1% 60D PU+30% Methanol+59.75% THF (CHX-CHA-AgSD-L-1,12 Dod)
5) 2% CHX+1.5% CHA+0.75% AgSD+1% 1,2 Tetradecanediol+1% Lactic acid+3% 93A PU+1% 60D PU+30% Methanol+59.75% THF (CHX-CHA-AgSD-L-1,14 TD)
6) 2% CHX+1.5% CHA+0.75% AgSD+1% 1,2 Octanediol+1% Lactic acid+3% 93A PU+1% 60D PU+30% Methanol+59.75% THF (CHX-CHA-AgSD-L-O)
7) 3.5% CHX+0.75% AgSD+1% 1,2 Octanediol+1% Lactic acid+3% 93A PU+1% 60D PU+30% Methanol+59.75% THF (CHX-AgSD-L-O)
8) 3.5% CHA+0.75% AgSD+1% 1,2 Octanediol+1% Lactic acid+3% 93A PU+1% 60D PU+30% Methanol+59.75% THF (CHA-AgSD-L-O)
9) 3.5% CHA+0.75% AgSD+3% 93A PU+1% 60D PU+30% Methanol+61.75% THF (CHA-AgSD)

To test bacterial adherence, the following experiments were performed.

Preparation of Agar Tract Model:

0.5% agar+20% bovine adult serum (BAS)+0.5% milk+0.03% trypticase soy broth (TSB) in phosphate buffered saline (PBS). The necessary amounts of agar and TSB were weighed and suspended in PBS with a magnetic stirring bar in the flask. The medium was sterilized by autoclaving at 121° C. for 20 min. After autoclaving, the medium was allowed to cool down to 45-48° C. in a water bath put on a magnetic stirrer. BAS and milk were warmed to room temperature. 5 ml of milk was mixed with 5 ml BAS in a sterile culture tube and added to the flask with gentle stirring. The remaining amount of BAS was added to the flask. The medium was maintained at 45-48° C. 2.5 ml aliquots of medium were dispensed in different culture tubes and allowed to solidify at room temperature.

Evaluation of Bacterial Adherence

Catheter segments, 4 cm long and sealed at both ends, were inserted vertically into the center of the medium in each tube with 0.5 cm of the catheter protruding out of the medium. The caps of each tube were sealed with Parafilm to prevent dessication. 5 catheter segments were used for each test. Untreated catheter segments were used as the control. After 30 minutes, each catheter segment was lifted up (approximately 0.5 cm) and 25 ul of the bacterial culture ($1-3 \times 10^8$ cfu/ml) was added on the catheter just near the surface of the medium so that the inoculum was also spread on medium surface. The catheter was then placed back to its original position and incubated at 37° C. for 7 days. The catheter segments were removed from the tubes and blotted on tissue. They were rinsed twice in 10 ml saline (6 segments/10 ml saline) and blotted dry. 0.5 cm was then cut off from both the ends of each catheter segment. Each catheter segment was then put in 4 ml LTSB (drug inactivating medium) in a culture tube and sonicated for 20 min. 0.5 ml aliquot from each tube was then plated out on TSA plates and incubated for 24-48 hours.

MRSA adherence On central venous catheter coated with various salts of Chlorhexidine along with silver salt and Octanediol was tested, using materials prepared as set forth above. To determine which Chlorhexidine salt would show better efficacy, catheters were coated with CHA, CHX, and a combination of CHA+CHX along with a silver salt and Octanediol and lactic acid was evaluated. Using MRSA as the test organism and adherence was evaluated 21 days post infection. The results are shown in TABLE 14.

TABLE 14

MRSA adherence (21 days after implantation and infection)

| Group | Adherence (Cfu/cm) | $Log_{10}$ Reduction from Control Counts |
|---|---|---|
| Control (uncoated catheters) | $3.8 \times 10^4$ | — |
| CHX-AgSD-L-O | 77 | 2.7 |
| CHX-CHA-AgSD-L-O | 38 | 3.0 |
| CHA-AgSD-L-O | $3.9 \times 10^2$ | 2.0 |
| CHA-AgSD-L | $6.1 \times 102$ | 1.8 |

These data indicate that the groups containing CHX or CHX+CHA showed higher activity than the groups with CHA alone.

To evaluate bacterial adherence to central venous catheter (CVC) segments coated with various alkanediols along with CHX-CHA-AgSD-L, experiments were performed using the impregnation solutions set forth in TABLE 15, below, which also shows the results of these experiments.

TABLE 15

P. aeruginosa adherence (10 days after implantation and infection)

| Group | Cfu/cm | $Log_{10}$ Reduction from Control Counts |
|---|---|---|
| Control (uncoated catheters) | $1.0 \times 10^4$ | — |
| CHA-AgSD | $3.4 \times 10^3$ | 0.52 |
| CHX-CHA-AgSD-L-O | $1.5 \times 10^2$ | 1.80 |
| CHX-CHA-AgSD-L-D | 20 | 3.20 |
| CHX-CHA-AgSD-L-1,2 Dod | 15 | 2.80 |
| CHX-CHA-AgSD-L-1,12 Dod | 18 | 2.70 |
| CHX-CHA-AgSD-L-TD | 32 | 2.50 |

These data indicate that each of the alkanediols tested enhanced the efficacy when used along with CHX-CHA-AgSD-L.

17. EXAMPLE 13

Bacterial Adherence to Impregnate Soft Tissue PTFE Patches

The following impregnation solutions were prepared:
0.1% Silver carbonate+0.3% CHA (S-CHA)
0.1% Silver carbonate+0.2% CHX+0.15% CHA (S-CHX-CHA)
0.1% Silver carbonate+0.2% CHX+0.15% CA (S-CHX-CHA)
0.1% Silver carbonate+0.2% CHX+0.15% CA+1% O (S-CHX-CHA-O)
0.1% Silver carbonate+0.2% CHX+0.15% CHA+1% D (S1-CHX-CHA-D)
0.05% Silver carbonate+0.2% CHX+0.15% CHA+1% D (S2-CHX-CHA-D)
(all of them contain 1% Lactic acid)
(S=Silver carbonate, D=1,2 Decanediol, O=1,2 Octanediol)

1 $cm^2$ pieces of PTFE soft tissue patches ("STPs") were soaked in solutions comprising about 60 percent THF (v/v), about 20 percent Methanol (v/v) and about 20 percent ammonium hydroxide (v/v) as well as the active agents indicated above, then suctioned using a vacuum pump and left for 5 minutes. The pieces were removed, dried and rinsed in water. After 24 hours the patches were tested.

To evaluate bacterial adherence to the STPs, the following experiments were performed. Several 3 piece sets of PTFE tissue patch from each group and unimpregnated control, each 1 $cm^2$, were soaked in medium containing 50% TSB+ 50% BAS (1 ml per 1 $cm^2$ of each piece) and placed on an orbital shaker at 37° C. Adherence was tested after seven days as follows: one set from each group was removed, and transferred to a fresh media containing $10^5$ cfu of organisms (1 ml/1 $cm^2$) and incubated for 24 hours at 37° C. The pieces were then removed and rinsed twice in saline at the rate of 2 ml/$cm^2$ by vortexing at low speed, blotted dry and suspended in drug inactivating media (4 ml/1 piece) and sonicated. 0.5 ml. aliquots were plated. Adherence after 14 days was tested as follows. patches were transferred to fresh media on the 7th day and continued orbital shaking for 14 days and then transferred to fresh media containing bacteria and processed as before. Adherence after 21 days was tested as follows: patches were transferred to fresh media on the 7th and 14th days with continuous shaking. On the 21st day, they were transferred to fresh media containing bacteria and processed as before.

The results obtained using different test organisms and after different periods of time are shown in TABLES 16-18, below.

TABLE 16

*P. aeruginosa* adherence (cfu/$cm^2$) on STPs 7 days after soaking in S. TSB

| Group | Adherence (cfu/$cm^2$) |
|---|---|
| Control | $2.0 \times 10^5$ |
| S-CHA | $6.0 \times 10^4$ |
| S-CHX-CHA | $5.0 \times 10^4$ |
| S-CHX-CHA-O | 630 |
| S-CHX-CHA-D | 43 |

TABLE 17

*S. aureus* adherence (cfu/$cm^2$) on STPs various days after soaking in S. TSB

| Group | Chlorhexidine level (ug/$cm^2$) | Bacterial Adherence (cfu/$cm^2$) | | |
|---|---|---|---|---|
| | | 7 day | 14 day | 21 day |
| Control | — | $2.3 \times 10^5$ | $1.9 \times 10^5$ | $3.6 \times 10^5$ |
| S-CHA | 86 | 0 | $1.2 \times 10^5$ | $2.6 \times 10^5$ |
| S-CHX-CHA | 94 | 0 | $1.2 \times 10^5$ | N.D |
| S1-CHX-CHA-D | 96 | 0 | 0 | $6.3 \times 10^1$ |
| S2-CHX-CHA-D | 94 | 0 | 73 | $3.4 \times 10^2$ |

ND = Not Determined

TABLE 18

*P. aeruginosa* adherence (cfu/$cm^2$) on STPs, various days after soaking in S. TSB

| Group | 7 day | 14 day |
|---|---|---|
| Control | $2.0 \times 10^5$ | $1.5 \times 10^6$ |
| S-CA | $6.0 \times 10^4$ | $3.7 \times 10^5$ |
| S-CX-CA | $5.0 \times 10^4$ | $3.0 \times 10^5$ |
| S1-CX-CA-D | 43 | $3.0 \times 10^4$ |
| S2-CX-CA-D | 101 | $3.1 \times 10^4$ |

18. EXAMPLE 14

Bacterial Adherence to Silicone Urinary Catheter Segments

Bacterial adherence to silicone urinary catheters impregnated using a two-step method with various alkanediols along with Chlorhexidine, Silver carbonate and Lactic Acid was evaluated.

Catheter segments were impregnated as follows.

Step 1: Catheters were soaked for 1 hour in 0.3% Triclosan (T) (w/v)+1.0% L (Lactic Acid) (v/v) in 30% Methanol (v/v)+ 68.7% (v/v) THF. The catheters were removed, dried for 1 hour, rinsed in water and dried for another hour.

Step 2: Catheters were dipped in the following solutions and dried for 24 hours and then used for testing.

CHX: 2% (w/v) CHX+15% (w/v) Silastic Medical Adhesive Type A+1% glycerin+82% (v/v) THF CHX-O: 2% (w/v) CHX+1% O+15% (w/v) Silastic Medical Adhesive Type A+1% glycerin+81% (v/v) THF CHX-D: 2% (w/v) CHX+1% D+15% (w/v) Silastic Medical Adhesive Type A+1% glycerin+81% (v/v) THF CHX-1,2Dod: 2% (w/v) CHX+1% 1,2 Dodecandiol+15% (w/v) Silastic Medical Adhesive Type A+1% glycerin+81% (v/v) THF CHX-1,12Dod: 2% (w/v) CHX+1% 1,12 Dodecanediol+ 15% (w/v) Silastic Medical Adhesive Type A+1% glycerin+ 81% (v/v) THF CHX-TD: 2% (w/v) CHX+1% TD+15% (w/v) Silastic Medical Adhesive Type A+1% glycerin+81% (v/v) THF Duration of resistance of adherence of bacteria on the catheters was tested in the in vitro urinary tract model described above in Section 12. The results are shown in TABLE 19.

TABLE 19

| Duration of activity against *S. aureus* | |
|---|---|
| Group * | (Days) |
| Control | 1 |
| T-CHX-L | 8 |
| T-CHX-L-O | 30 |
| T-CHX-L-D | >50 |
| T-CHX-L-1,2 Dod | >50 |
| T-CHX-L-1,12 Dod | >50 |
| T-CHX-L-TD | >50 |

* The letters for each catheter group denote the anti-infectives in the catheter These data indicate that silicone urinary catheters containing alkanediols along with T+CHX+L showed longer activity than T+CHX+L.

19. EXAMPLE 15

Bacterial Adherence to Impregnated Wound Dressings

Wound dressings were impregnated with the following solutions:

| Ingredients | (% w/w) |
|---|---|
| *Antimicrobial composition 1* | |
| CHA | 0.15 |
| CHX | 0.15 |
| AgSD | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |
| *Antimicrobial composition 2* | |
| CHA | 0.15 |
| CHX | 0.15 |
| AgSD | 0.30 |
| Lactic Acid | 0.50 |
| 1,12 Dodecanediol | 0.50 |
| Polyurethane 93A | 0.40 |
| Polyurethane 60D | 0.10 |
| Methanol | 30.00 |
| Tetrahydrofuran | 67.90 |
| *Antimicrobial composition 3* | |
| CHA | 0.15 |
| CHX | 0.15 |
| Silver Carbonate | 0.30 |
| Lactic Acid | 0.50 |
| 1,2 Decanediol | 0.50 |
| Polyurethane 93A | 0.40 |
| Polyurethane 60D | 0.10 |
| Methanol | 30.00 |
| Tetrahydrofuran | 67.90 |
| *Antimicrobial composition 4* | |
| Polyhexamethylene biguanide | 0.30 |
| Silver Carbonate | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 67.90 |
| *Antimicrobial composition 5* | |
| CHA | 0.15 |
| CHX | 0.15 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |
| *Antimicrobial composition 6* | |
| Polyhexamethylene biguanide | 0.30 |
| 1,2 Decanediol | 0.50 |
| Lactic Acid | 0.50 |
| Polyurethane 93A | 0.40 |
| Polyurethane 60D | 0.10 |
| Methanol | 30.00 |
| Tetrahydrofuran | 68.20 |

Wound dressings (Dukal Non-Adherent Pad) were dipped into the antimicrobial impregnation solution and dried for 24 hours. The dressings were cut into 1 cm² pieces and the Zones of Inhibition against various bacteria were determined. For the Zones of Inhibition Test, 1 cm² piece of each dressing was placed on a Trypticase Soy Agar plate seeded on the surface with 0.3 mL of $10^8$ colony forming units (CFU)/mL of the test organism. The plates were incubated at 37° C. for 24 hours. The Zone of Inhibition around the dressing was measured. The results are shown in TABLE 20, below.

TABLE 20

| Zone of Inhibition (mm) testing of Dressings treated with Antimicrobial Composition (AC) 1, 2, 5 and 6 | | | | | | | | |
|---|---|---|---|---|---|---|---|---|
| | AC 1 | | AC 2 | | AC 5 | | AC 6 | |
| Organism | Day 1 | Day 2 | Day 1 | Day 2 | Day 1 | Day 2 | Day 1 | Day 2 |
| *S. aureus* | 15.0 | 15.0 | 15.0 | 15.0 | 14.5 | 11.0 | 13.5 | 6.5 |
| MRSA | 15.5 | 14.0 | 15.0 | 12.5 | 14.5 | 10.5 | 13.0 | 6.5 |
| *P aeruginosa* | 14.0 | 14.0 | 15.0 | 15.0 | 13.0 | 5.5 | 8.5 | 5.5 |
| *C. albicans* | 16.0 | 13.0 | 16.0 | 13.0 | 15.5 | 9.0 | 12.0 | 7.0 |

These data indicate that dressings impregnated with antibacterial agents and alkanediols exhibit broad spectrum antimicrobial activity.

Various publications are cited herein, the contents of which are incorporated by reference in their entireties.

What is claimed:

1. A composition for preparing a bio-film resistant surface comprising
    (i) an antimicrobial composition consisting of a biguanide present at between about 0.1 and 5 percent (weight/volume), an alkanediol present at between about 0.5 and 5 percent (volume/volume), and one or more hydroxy acid present at between about 0.5 and 3 percent (volume/volume), wherein the alkanediol and hydroxy acid are present in amounts that increase the antimicrobial effect of the biguanide and
    (ii) a solvent selected from the group consisting of an alcohol, tetrahydrofuran, and mixtures thereof.

2. The composition of claim 1, wherein the biguanide is selected from the group consisting of chlorhexidine free base, chlorhexidine diacetate, chlorhexidine gluconate, polyhexamethylene biguanide, and a mixture thereof.

3. The composition of claim 1, wherein the alkanediol is selected from the group consisting of octanediol, 1,2-decanediol, 1,2-dodecanediol, 1,12-dodecanediol and 1,2 tetradecanediol.

4. The composition of claim 1, further comprising an additional antimicrobial agent in an amount between about 0.05 and 3 percent (weight/volume).

5. The composition of claim 4, wherein the additional antimicrobial agent is a silver compound.

6. The composition of claim 5, wherein the silver compound is silver sulfadiazine.

7. The composition of claim 1, wherein the hydroxy acid is selected from the group consisting of lactic acid, citric acid, and salicylic acid.

8. The composition of claim 1, comprised in a wipe.

9. The composition of claim 2, comprised in a wipe.

10. The composition of claim 3, comprised in a wipe.

11. The composition of claim 4, comprised in a wipe.

12. The composition of claim 5, comprised in a wipe.

13. The composition of claim 6, comprised in a wipe.

14. The composition of claim 7, comprised in a wipe.

15. The composition of claim 1, comprised in a wound dressing.

16. The composition of claim 2, comprised in a wound dressing.

17. The composition of claim 3, comprised in a wound dressing.

18. The composition of claim 4, comprised in a wound dressing.

19. The composition of claim 5, comprised in a wound dressing.

20. The composition of claim 6, comprised in a wound dressing.

21. The composition of claim 7, comprised in a wound dressing.

22. The composition of claim 1, further comprising a polymer.

23. The composition of claim 22, comprised in a wipe.

24. The composition of claim 22, comprised in a wound dressing.

25. The composition of claim 4, wherein the additional antimicrobial agent is a chlorinated phenol.

26. The composition of claim 4, wherein the additional antimicrobial agent is triclosan.

* * * * *